US011051740B2

(12) United States Patent
Pemberton et al.

(10) Patent No.: US 11,051,740 B2
(45) Date of Patent: Jul. 6, 2021

(54) SYSTEM AND METHOD FOR RAPID ECG ACQUISITION

(71) Applicant: GE Precision Healthcare LLC, Wauwatosa, WI (US)

(72) Inventors: Matthew Lane Pemberton, Wauwatosa, WI (US); Brian Joseph Young, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 191 days.

(21) Appl. No.: 16/371,814

(22) Filed: Apr. 1, 2019

(65) Prior Publication Data

US 2019/0223741 A1   Jul. 25, 2019

Related U.S. Application Data

(63) Continuation of application No. 15/189,810, filed on Jun. 22, 2016, now Pat. No. 10,278,602.

(51) Int. Cl.
*A61B 5/318* (2021.01)
*A61B 5/316* (2021.01)
(Continued)

(52) U.S. Cl.
CPC .............. *A61B 5/316* (2021.01); *A61B 5/276* (2021.01); *A61B 5/318* (2021.01); *A61B 5/339* (2021.01); *A61B 5/349* (2021.01); *A61B 5/6843* (2013.01); *A61B 5/7203* (2013.01); *A61B 5/7221* (2013.01); *A61B 5/746* (2013.01); *A61B 2505/01* (2013.01)

(58) Field of Classification Search
CPC ... A61B 5/7203; A61B 5/0402; A61B 5/7221; A61B 5/318; A61B 5/333
See application file for complete search history.

(56) References Cited

U.S. PATENT DOCUMENTS 5,873,838 A  2/1999  Mogi
6,754,517 B2  6/2004  Nissila et al.
(Continued)

FOREIGN PATENT DOCUMENTS

JP    08229014 A    9/1996
WO    2004075738 A2    9/2004

OTHER PUBLICATIONS

International Search Report and Written Opinion for PCT/US2017/037423, dated Aug. 22, 2017, 20 pages.

*Primary Examiner* — George R Evanisko
(74) *Attorney, Agent, or Firm* — Andrus Intellectual Property Law, LLP

(57) ABSTRACT

In one embodiment, an ECG monitoring system includes two or more electrodes configured to record cardiac potentials from a patient, at least one processor, and a rapid acquisition module executable on the at least one processor to: determine that an impedance of each electrode is less than an impedance threshold; record initial ECG lead data based on the cardiac potentials; determine that a noise level in each ECG lead of the initial ECG data is less than a noise threshold; start a recording timer once the noise level is below the noise threshold; record an ECG dataset while the noise level is maintained below the noise threshold until the recording timer reaches a predetermined test duration; store the ECG dataset and provide a completion alert.

15 Claims, 5 Drawing Sheets

(51) Int. Cl.
*A61B 5/00* (2006.01)
*A61B 5/276* (2021.01)
*A61B 5/339* (2021.01)
*A61B 5/349* (2021.01)

(56) References Cited

U.S. PATENT DOCUMENTS

| | | |
|---|---|---|
| 7,123,953 B2 | 10/2006 | Starobin et al. |
| 7,142,924 B2 | 11/2006 | Legay et al. |
| 8,560,054 B2 | 10/2013 | Badilini |
| 10,278,602 B2 * | 5/2019 | Pemberton ............ A61B 5/6843 |
| 2004/0186388 A1 | 9/2004 | Gerasimov |
| 2008/0208129 A1 | 8/2008 | Carter et al. |
| 2014/0343392 A1 | 11/2014 | Yang |

* cited by examiner

SYSTEM AND METHOD FOR RAPID ECG ACQUISITION

CROSS REFERENCE TO RELATED APPLICATION

This application is a continuation of U.S. patent application Ser. No. 15/189,810, filed Jun. 22, 2016, which is incorporated herein by reference in entirety.

BACKGROUND

This disclosure generally relates to medical monitoring systems and devices, and more specifically to a method and system for ECG monitoring.

Electrocardiograms (ECGs) are graphic depictions of electrical activity in the heart. ECGs are produced by electrocardiographs which are available as stand alone devices, portable devices, and/or as integrated functions in various types of multi-vital sign monitoring devices. ECGs are depicted by time (ms) versus voltage (μV) and typically are represented as a waveform. The typical five important aspects, or portions, of an ECG waveform are the P wave, QRS complex (represented as the combination of the Q, R, and S waves respectively), and T wave. The less frequently seen sixth portion is a U wave. The data produced from the graphical depictions are useful in diagnosis of patients to determine what, if any, and the extent to which heart-related problems exist in a patient. For instance, ECGs are used in diagnosing: cardiac arrhythmias (irregular heart rhythms), myocardial infarction (heart attacks), hyper- and hypokalemia (high or low potassium levels, respectively), blockage, ischemia (loss of oxygen due to lack of blood flow possibly from blockage), just to name a few, and may also assist in diagnosis of non-heart related ailments. Accordingly, ECGs are known and proven to be valuable tools in diagnosis heart and even non-heart-related problems with patients.

Particularly, the ECG waveforms are useful in determining whether certain conditions exist or the predisposition of such conditions occurring based on established patterns. Particularly, important information can be derived by measuring the time between certain waveforms; commonly reviewed time intervals are those between the P wave and the beginning of the QRS interval (known as the PR interval) and the time between the QRS complex and the T wave (known as the QT interval. Other relevant data may be derived from the PR segment, the QRS complex, and the ST segment.

Typically, ECGs are used as diagnostic tools in various settings, such as hospitals and doctors offices. Oftentimes, it is important for reliable ECGs to be obtained as quickly as possible, such as in emergency situations or even in busy clinical settings.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, an ECG monitoring system includes two or more electrodes configured to record cardiac potentials from a patient, at least one processor, and a rapid acquisition module executable on the at least one processor to: determine that an impedance of each electrode is less than an impedance threshold; record initial ECG lead data from each lead in a predefined lead set among the two or more electrodes; determine that a noise level in the ECG data recorded in each lead is less than a noise threshold; start a recording timer once the noise level is below the noise threshold; record an ECG dataset while the noise level is maintained below the noise threshold until the recording timer reaches a predetermined test duration; store the ECG dataset and provide a completion alert.

One embodiment of a method of monitoring ECG includes determining that an impedance of each of two or more electrodes is less than an impedance threshold and recording an initial ECG lead data with a processor from each lead in a predefined lead set between the two or more electrodes. The method further includes determining that a noise level in the initial ECG lead data recorded in each lead is less than a noise threshold, starting a recording timer once the noise level is below the noise threshold, and recording an ECG dataset while the noise level is maintained below the noise threshold until the recording timer reaches a predetermined test duration. The ECG dataset is then stored in memory and a completion alert is generated.

Another embodiment of an ECG monitoring system includes a means for determining that an impedance of each electrode is less than an impedance threshold and that a noise level in an initial ECG lead data recorded from each lead in a lead set is less than a noise threshold. The ECG monitoring system further includes a means for automatically recording an ECG dataset of a predetermined test duration while the impedance is maintained below the impedance threshold and the noise level is maintained below the noise threshold. The ECG monitoring system further includes a means for storing the ECG dataset in memory and a means for generating a completion alert.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
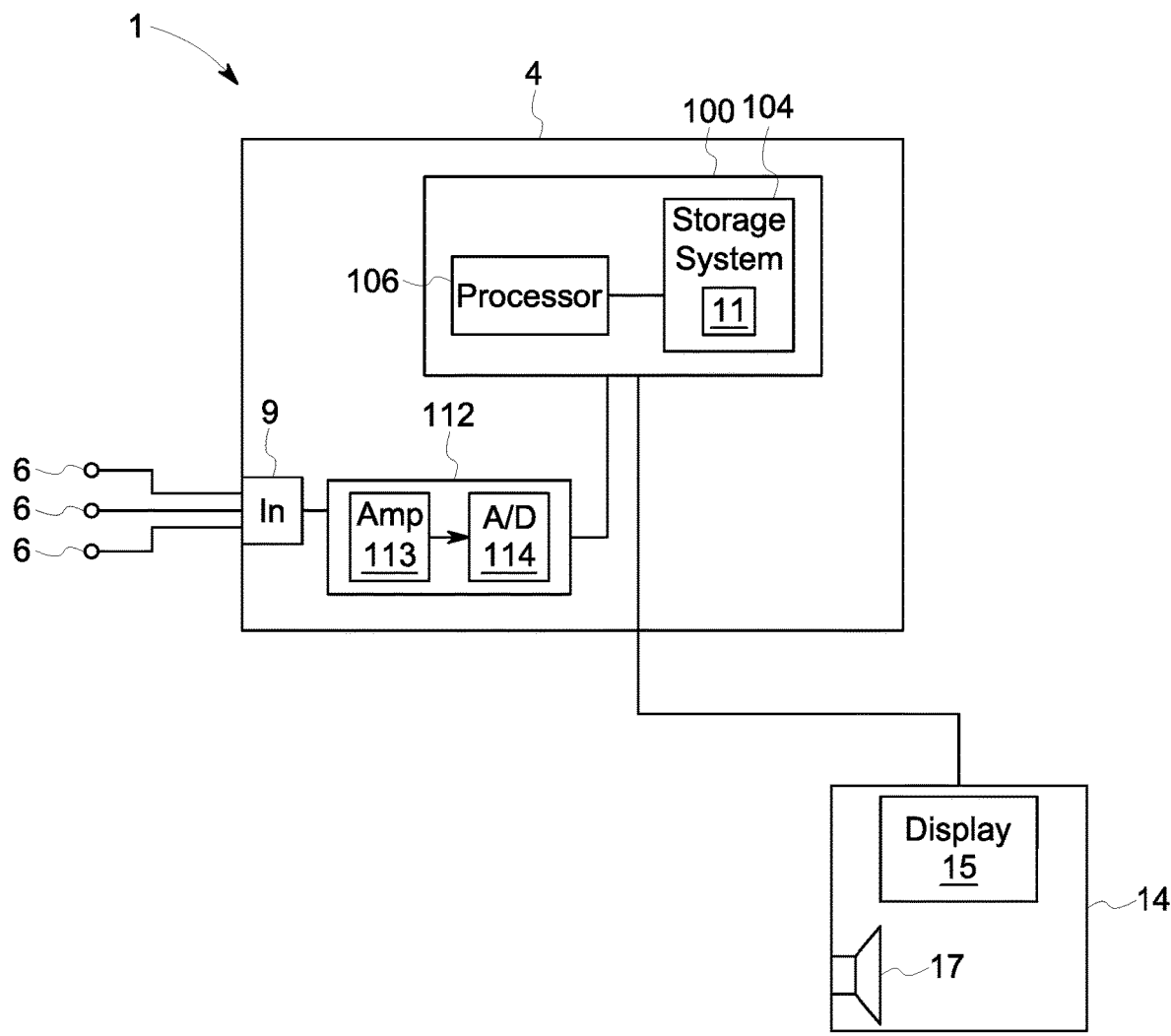
FIG. 1 depicts one embodiment of an ECG monitoring system according to the present disclosure.

Through their experimentation and research in the relevant field, the present inventors have recognized that a need exists in the relevant field for an ECG monitoring system and method that collects and obtains reliable ECG data as quickly as possible. Currently available ECG monitoring systems and methods may offer functionality that locates and extracts optimal ECG data from a large ECG dataset 40, such as where cardiac potentials are recorded over a period of time, such as a period of minutes, and the data is reviewed to select the best portion upon which to perform cardiac-related data analysis. This method of performing a test often requires the user to acquire more data than is necessary and be attentive to observing the waveform so that they are confident to have sufficient data quality. Such systems often take too long to obtain the needed ECG data and also require too much involvement by the clinician performing the test.

A person having ordinary skill in the art will recognize that all ECG electrodes require a period of time to obtain a good connection between the patient's skin and the electrodes, often referred to as "settling time." During settling time, the noise level in the leads will be higher, and as the electrodes settle the noise level will decrease. The interface impedance between the patient and the electrode, and thus the noise level, reduces relatively rapidly in the first few minutes after application, and the values tend to level out after the settling time. Several variables play into the amount of settling time required before reliable ECG data can be obtained, such as electrode type, a patient's skin chemistry, a patient's age, a patient's condition (such as whether they have poor circulation, are sweating, etc.), or the like.

In currently available systems, a clinician must monitor the ECG waveforms on the patient in order to determine when the settling process has completed and the ECG recording can commence. Further, it may not always be easy or possible for a clinician to immediately determine when the settling period has completed and the noise level due to electrode impedance has reached an adequate level for recording to commence. The inventors have recognized that this task of monitoring leads during the electrode settling process occupies valuable clinician time and attention, which could be directed to other tasks.

The inventors have recognized that a system for rapid identification of when the settling has sufficiently completed in order to obtain reliable ECG data can expedite the ECG testing process, not only to eliminate unnecessary waiting time where the clinician is unable to immediately identify that the settling process has sufficiently complete, but to eliminate incidents where retests are required as a result of performing the test prematurely. In emergency room settings, for example, premature data acquisition can cause significant delays because the clinician often is unable to determine that the ECG data is unreliable until after completion of the ECG test and analysis of the ECG dataset. At that point, the test will need to be redone and significant time is wasted. Accordingly, the inventors have developed the disclosed system based further on their recognition of this problem in order to guarantee that you will end up with clean data as quickly as possible.

Accordingly, in view of their recognition of the shortcomings of presently available ECG monitoring systems and methods and the recognition of a need for an ECG monitoring system and method that that automatically recognizes when the settling process is completed and obtains reliable ECGs as quickly as possible and with minimal involvement by a clinician, the presently disclosed system and method was developed. For example, the systems and methods disclosed herein automatically monitor the signal quality in each lead to provide the earliest available ECG meeting certain predefined quality standards.

As disclosed herein, the ECG monitoring system and method, which may be embodied in a software program, operates to automatically obtain the earliest reliable ECG dataset 40, and to automatically analyze the ECG dataset 40 without the need for intervention by the clinician. A completion alert is provided or automatically presented to the clinician when the test is completed, which may include presenting the analysis results. Accordingly, a clinician using the presently disclosed system and method can connect the electrodes to the patient and then turn their attention to other tasks relating to the patient care, such as administrative tasks involved in the ECG testing process. The system then automatically determines when the electrodes have reached their settling point and when the earliest reliable ECG data can be obtained, and then automatically records and analyses the first available reliable ECG data. In certain embodiments, the system and method may include running a settling timer that monitors how long the system looks for reliable ECG data and provides a failure alert to a clinician if reliable data is not located within a predetermined attempt duration, which may be adjustable by a user to be appropriate for the clinical setting in which the method and system is employed.

FIG. 1 depicts one embodiment of an ECG monitoring system 1 comprising three ECG electrodes 6 connected to an input port 9 of a monitor 4. While the example of FIG. 1 depicts an embodiment including three electrodes, a person of ordinary skill in the art will understand in light of this disclosure that the system 1 may include any number of two or more electrodes, and that common electrode arrangements for standard diagnostic ECGs include anywhere from three to fourteen electrodes with 10 electrodes being the most commonly used electrode configuration for diagnostic ECGs. As described in more detail herein, the system 1 also includes a user interface 14 connected to the monitor 4 to receive control inputs from a user, such as a clinician administering an ECG to a patient, and to provide auditory or visual outputs to the user. Accordingly, the user interface 14 including a display 15 and a speaker 17. The user interface 14 may be a separate device that is electrically or wirelessly connected to the monitor, or the user interface 14 may be integrated with the monitor 4, such as within the same housing. Alternatively, the user interface may include a printer that may be used as an output device to produce a printed form of the ECG dataset as the display.

The cardiac potentials recorded by the electrodes 6 are then processed by the signal processing circuit 112, which includes one or more amplifiers 113 and one or more analog-to-digital converters 114. For example, the amplifier 113 may be a differential amplifier that compares potentials measured by various electrodes 6, or compares the potentials measured at each electrode to a reference input (such as ground or an active drive voltage) to derive a signal which is then utilized by the computing system 100 to generate the ECG lead signals. The output from the amplifier 113 is digitized by the analog-to-digital converter (A/D converter) 114. The A/D converter 114 may be any device or logic set capable of digitizing analog physiological signals at an appropriate sampling rate. For example, the A/D converter 114 may be an analog front end (AFE). The signal processing circuit 112 may include multiple amplifiers 113 and A/D converters 114, such as one for each electrode in the system 1. For example, a 10 electrode set is configured so that one electrode is connected to a ground reference and the remaining 9 electrodes are used as inputs to 8 amplifiers and are digitized by 8 A/D converters to generate signals from which a standard 12-lead ECG is derived.

The output of the signal processing circuit 112 is received by the computing system 100 within the monitor 4. The computing system 100 includes one or more processors 106 and storage system 104 comprising computer memory. A rapid acquisition module 11 is stored within storage system 104, which is a set of software instructions executable by the processor 106 to determine when the electrodes have settled and automatically record an ECG dataset 40 of a predetermined length, or test duration, at the earliest time when valid and reliable ECG data is available.

In one embodiment, the rapid acquisition module 11 further receives an impedance of each electrode 6 and is executable on the processor 106 to determine that the impedance of each electrode is less than an impedance threshold. A person of ordinary skill in the art reviewing this disclosure will understand that impedance is typically measured between each sensing electrode and a reference electrode. As an example, in many electrode configurations the right leg (RL) electrode is connected to ground or an active drive circuit and serves as the reference point from which the impedance of the remaining electrodes is measured. The impedance threshold is a predetermined impedance amount below which the electrode can be assumed to be fully attached, or fixed, to a patient, such as adhered to a patient's skin. In various embodiments, a single impedance threshold may be set for each and every electrode 6 in the ECG monitoring system 1, or various impedance thresholds may be set for various electrode locations or electrode types, such as to account for expected variances in impedance at different locations on the patient's body or types of electrodes that may be used on the patient's body in particular applications.

Once the rapid acquisition module 11 determines that the impedance 32 of each electrode 6 is less than the impedance threshold, then it begins to generate initial ECG lead data based on the cardiac potentials obtained from each electrode 6. The initial ECG lead data may include all of the predefined set of ECG leads generated for the ECG (e.g., all 12 leads in a 12-lead ECG), or may be a predetermined subset thereof that is representative of the ECG dataset or most critical for obtaining a reliable ECG test (e.g., only the precordial leads or some other subset of the 12 leads are assessed for the noise level determination). The rapid acquisition module 11 further includes instructions executable to calculate a noise level in the initial ECG lead data, and compare the calculated noise level to a noise threshold. Accordingly, the rapid acquisition module 11 determines when a noise level in the initial ECG lead data recorded in each lead is less than the noise threshold. For example, the noise level determination may include calculation of a signal-to-noise ratio and determination that the signal-to-noise ratio is less than a threshold signal-to-noise ratio. For instance, the determination of the signal-to-noise ratio may include measurement of the QRS amplitude compared to a noise amplitude. The noise threshold value may be set the same for each lead, or various noise thresholds may be set for the leads in the predefined lead set, such as to account for various noise levels that might be expected in certain leads and/or applications.

The goal within the rapid acquisition module 11 is to determine when the settling process is complete and when is the earliest appropriate time to record an ECG dataset 40. In certain embodiments where the need for an immediate ECG dataset 40 outweighs the need for clean data in each lead, the rapid acquisition module 11 may be configured to begin recording an ECG dataset 40 when the noise level in just a subset of the leads in the lead set are below the respective noise thresholds Once the rapid acquisition module 11 has recognized that sufficient signal quality is presented in the respective leads, a recording timer is started and the rapid acquisition module 11 begins gathering an ECG dataset 40, with the aim of gathering data for a predetermined test duration while the signal quality remains good. The test duration 34 may be set by the clinician prior to or upon connecting the electrode 6 to the patient, or it may be a fixed standard value, such as a ten second ECG recording. Once an ECG dataset 40 has been automatically recorded that meets the noise level requirements, such as while the noise level in each lead is less than the noise threshold for that lead and/or below a general noise level threshold set for all leads, the ECG dataset 40 is stored, such as within the memory of the storage system 104, and a completion alert 42 is provided. For example, the completion alert 42 may be an auditory alert via the speaker 17, or a visual alert on the display 15. For example, the completion alert 42 may comprise or include automatically displaying the ECG dataset 40 on the display 15 for assessment by the clinician. Alternatively or additionally, the completion alert 42 may comprise a textual or other visual alert notifying the clinician that an ECG dataset 40 has been acquired, and such alert may require the clinician to take affirmative action to view the ECG dataset 40 and/or analysis results 44 determined therefrom. In one embodiment, the rapid acquisition module 11 automatically and immediately analyses the ECG dataset 40 upon completion of the recording, and such analysis results may be immediately provided to the clinician after generation of the completion alert 42 or as part of the completion alert 42.

The rapid acquisition module 11 may further be configured to receive an acceptance or rejection 38 of the ECG dataset 40 from the clinician. For example, the rapid acquisition module 11 may control the display 15 to present an option to the clinician to accept or reject the ECG dataset 40 that was automatically recorded. For example, such acceptance or rejection 38 inputs may be provided by the clinician through user interface 14. If the rapid acquisition module 11 receives a rejection 38 of a recorded ECG dataset 40, it may restart the recording timer and record a second ECG dataset, again executing instructions to find the first available dataset 40 of the test duration 34 that meets the noise threshold requirements. A second completion alert is then generated and the clinician can again accept or reject the second ECG dataset 40.

The rapid acquisition module may be configured so that it only attempts to automatically record an ECG dataset for a predetermined attempt duration, which may be adjustable by a user via the user interface 14. Specifically, the user may input an attempt duration 36 before or upon connecting the electrode 6 to the patient, and thereby can customize the rapid acquisition module 11 based on the situation or setting in which the ECG monitoring system 1 is being used. For example, in an emergency setting, the attempt duration may be set low, such as to five minutes or less, and in a clinical setting may be set higher, such as to ten minutes, fifteen minutes, or more. The attempt duration 36 may further be set by the clinician based on the type of electrodes that are being employed because different electrode types have different settling times, or based on the patient's condition. To this end, the rapid acquisition module 11 may be executable to start a settling timer once the impedance of each electrode 6 is determined to be less than the impedance threshold, and thus once the electrodes 6 are determined to be fully connected to the patient. Upon starting the settling timer, the rapid acquisition module 11 begins recording the initial ECG lead data from each lead and assessing the noise level and/or other signal quality measures as described above. In the instance where no ECG dataset 40 is obtained before the settling timer reaches the attempt duration, the rapid acquisition module 11 may generate a failure alert 46, which may be an auditory alert via speaker 17 or a visual alert provided on the display 15. Further, the rapid acquisition module 11 may further be configured to automatically record an ECG dataset once the settling timer reaches the attempt duration. For example, upon expiration of the attempt duration, the rapid acquisition module 11 may start the recording timer and record the ECG dataset 40 until the recording timer reaches the test duration. In another embodiment, once the attempt duration has expired, the rapid acquisition module 11 may examine a buffer of the recently recorded data to find the section of data having a length equal to the test duration that is the least noisy section of data, e.g., having the lowest signal-to-noise ratio across all of the leads or in designated key leads. The recording timer and the settling timer may be executed by the rapid acquisition module utilizing a timer circuit, such as a 555 timer integrated circuit, or may utilize the clock associated with the processor 106.

The system 1 may further be configured to provide the clinician, or user, with a means of overriding the automatic recording feature and forcing an immediate recording of and ECG dataset 40 of the predetermined test duration, such as providing a button or location on the user interface 14 through which the clinician can instruct immediate recording.

Figure 3:
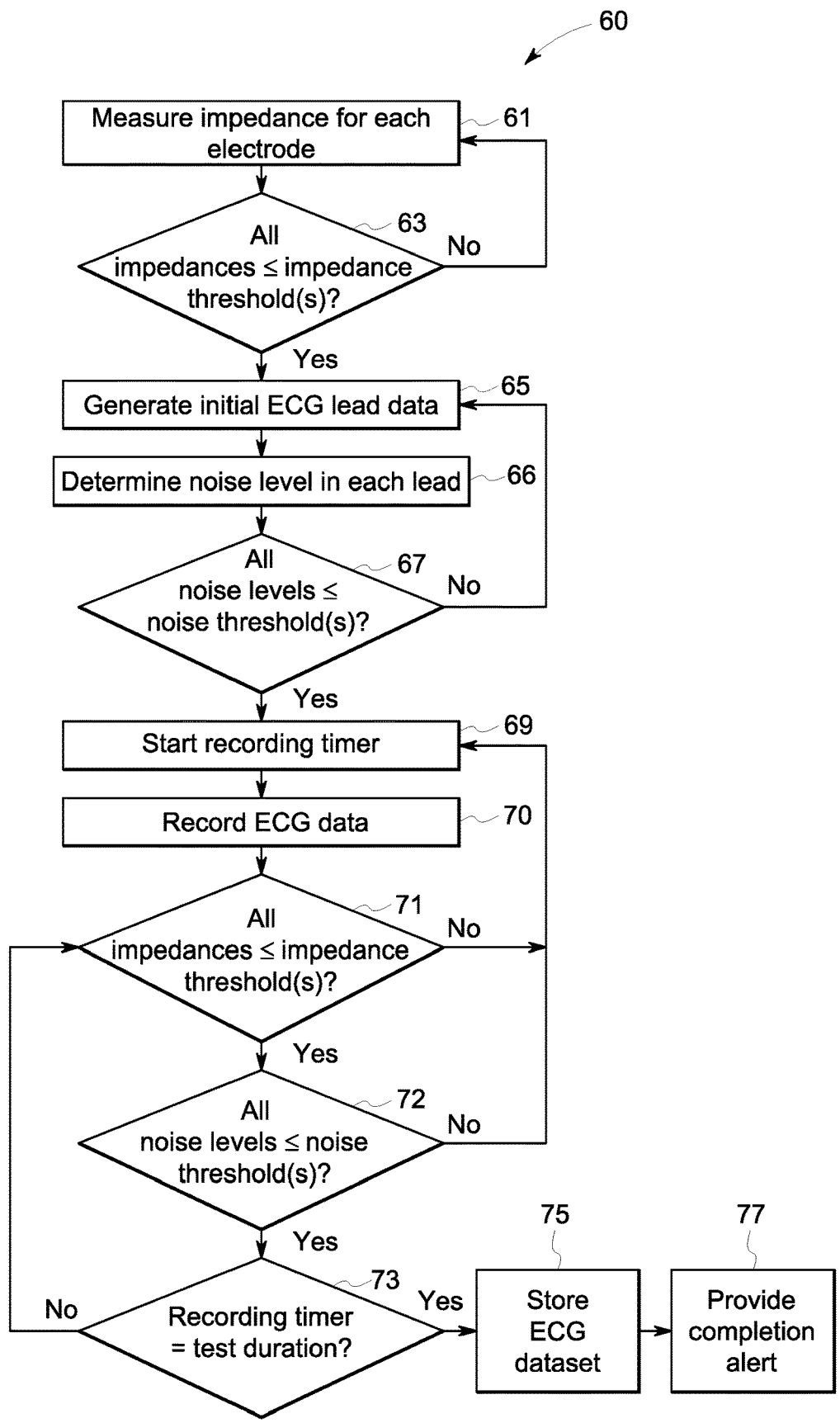
FIG. 3 depicts one embodiment of a method of monitoring ECG according to the present disclosure.

FIG. 3 depicts one embodiment of a method 60 of monitoring ECG, such as steps carried out by executing the instructions of the rapid acquisition module 11. At step 61, the impedance is measured for each electrode At step 63, it is determined whether all impedances are less than or equal to respective impedance thresholds. If not, then it is assumed that all electrodes 6 are not yet connected to the patient, and the rapid acquisition module 11 awaits further impedance measurements until all impedances are less than or equal to the impedance thresholds. Once the impedance threshold requirements are met, initial ECG lead data is recorded at step 65 and analyzed at step 66 to determine a noise level in each lead. At step 67, the rapid acquisition module 11 determines whether all noise levels are less than or equal to noise thresholds. If not, then further initial ECG lead data is recorded and a noise level assessed in each lead until all noise levels in the various leads are less than or equal to the respective one or more noise thresholds. A recording timer is then started at step 69 and ECG data is recorded at step 70. Step 71 determines whether all impedances remain less than or equal to the impedance thresholds, and step 72 determines whether all noise levels remain less than or equal to the noise thresholds. If either of those conditions are not met, then the recording timer is restarted at step 69 and process begins again at step 70 with recording new ECG data. If, on the other hand, all impedances are maintained below the impedance thresholds and all noise levels are maintained below the noise threshold, the rapid acquisition module 11 checks at step 73 whether the recording timer has reached the test duration. If not, it continues to check the impedance levels and noise levels against the respective threshold until the test duration is reached. Once the test duration is reached at step 73, then the ECG data set has been recorded and is then stored at step 75. A completion alert is then provided at step 77.

Figure 4A:
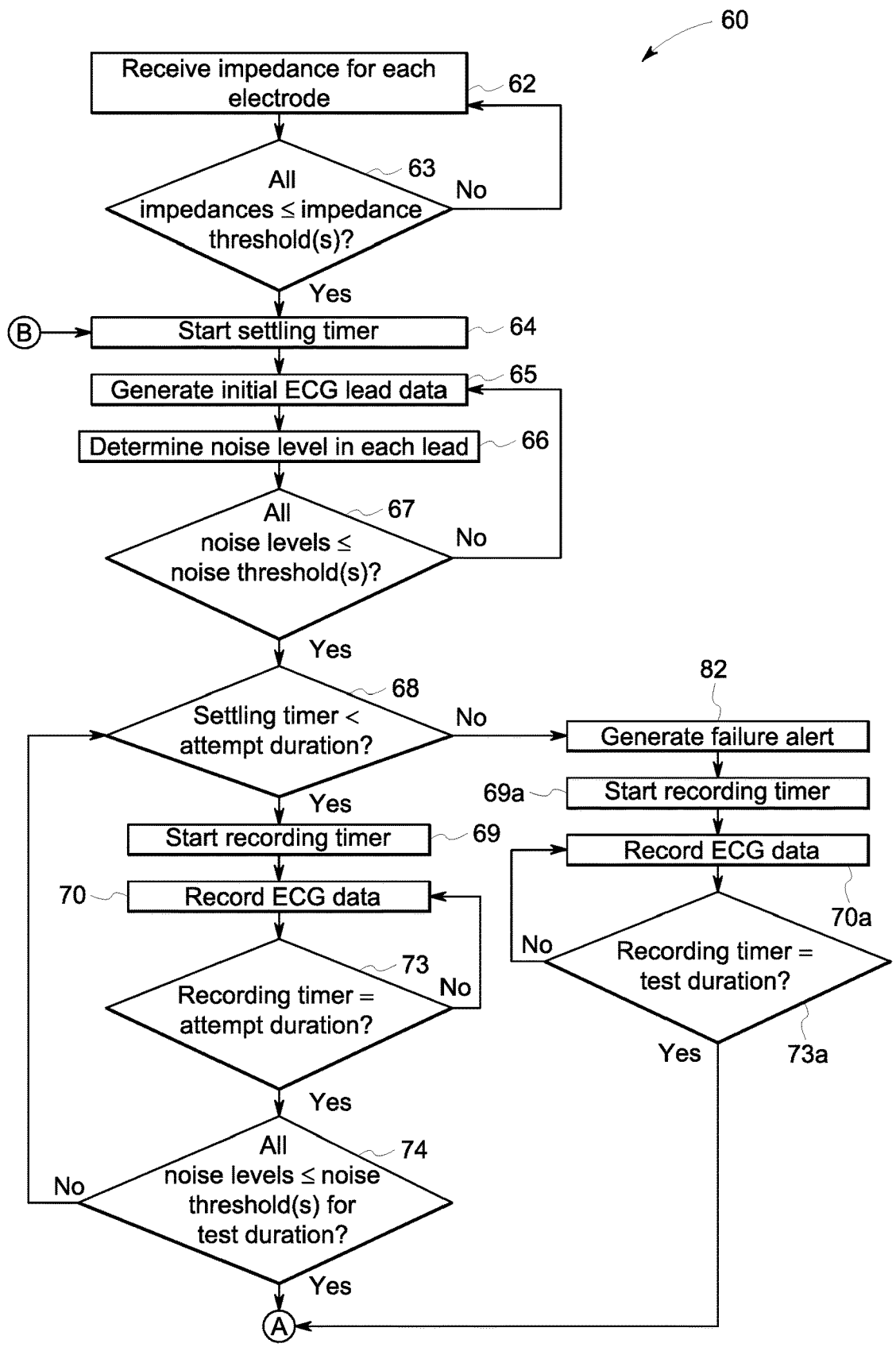
FIGS. 4A and 4B depict another exemplary embodiment of a method of monitoring ECG according to the present disclosure.
Figure 4B:
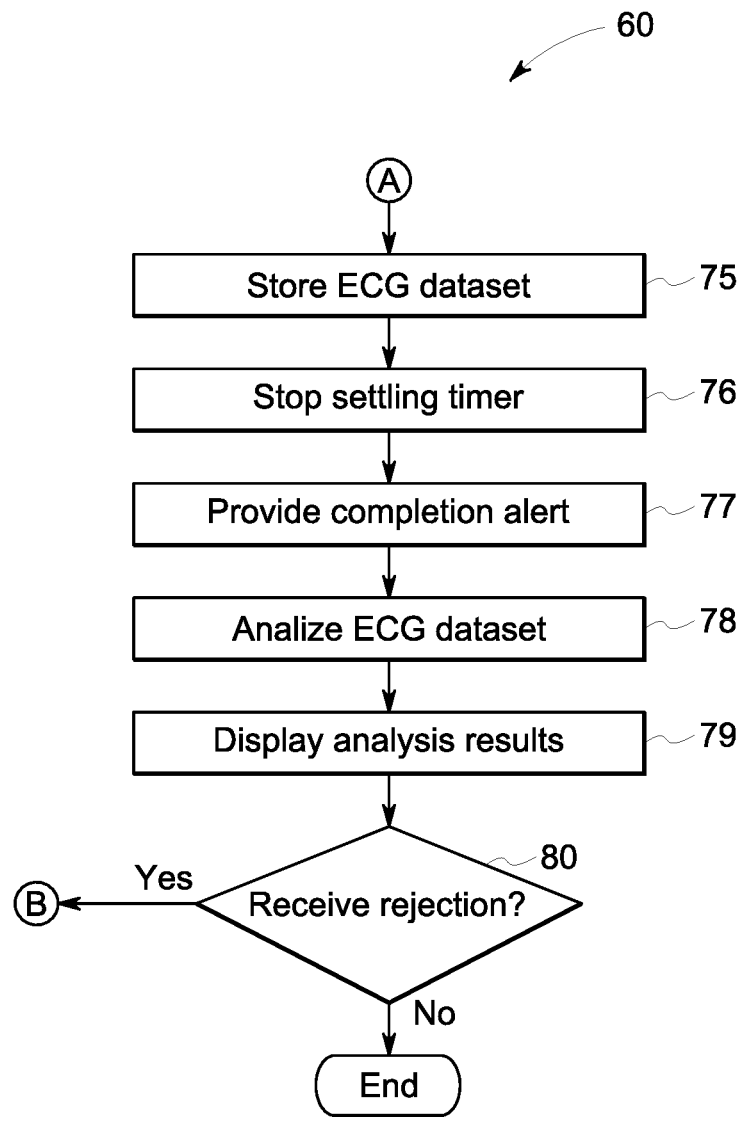

FIGS. 4A and 4B depict another embodiment of a method 60 of monitoring ECG. Impedance values for each electrode are received at step 62, and all impedances are compared to impedance thresholds at step 63 as described above. The impedance values are continually checked until all impedances are less than or equal to the respective impedance thresholds. At that point, the settling timer is started at step 64 and initial ECG lead data is recorded at step 65. A noise level is determined for the data in each lead at step 66, such as by calculating a signal-to-noise ratio for each lead. The noise level for each lead is then compared to a respective noise threshold at step 67 until all noise levels are less than or equal to the noise thresholds. Step 68 assesses whether the settling timer has reached the attempt duration, and if not then a recording timer is started at step 69 and ECG data is recorded at step 70. In the depicted embodiment, the ECG data is recorded for the test duration, and once the recording timer equals the test duration at step 73, the recorded data is analyzed to determined at step 74 whether all noise levels remained less than or equal to the noise thresholds for the test duration. For example, the signal-to-noise ratio for the data in each lead may be compared to threshold values to make that determination. If the data exceeds the noise threshold requirement, then the rapid acquisition module 11 returns to step 68 to see if the settling timer has reached the attempt duration. If not, then the recording timer is restarted and a new ECG dataset is recorded and assessed.

If an ECG data set that meets the noise threshold is not recorded during the attempt duration and the settling timer reaches the attempt duration at step 68, then a failure alert is generated at step 82. The recording timer is then started at step 69*a* and ECG data is recorded at step 70*a* until the recording timer equals the test duration at step 73*a*. In this situation, the recorded data may then be accepted as the ECG dataset 40 regardless of noise since a dataset meeting the noise threshold was unable to be recorded.

Once the ECG dataset 40 is recorded, it is stored at step 75 and the settling timer is stopped at step 76. A completion alert is provided at step 77, such as an audio and/or visual alert provided via the user interface 14. The ECG dataset is analyzed at step 78 and analysis results are presented at step 79, such as on the display 15 of the user interface 14. The clinician may then enter an acceptance or rejection of the ECG dataset 40 at step 80, such as via user interface 14. If a rejection is received at step 80, then the rapid acquisition module 11 may restart the settling timer at step 64 and re-execute the steps to assess the noise levels in each lead and attempt to re-record a reliable ECG dataset 40. If, on the other hand, a rejection is not received at step 80, then the method is completed, and the ECG dataset 40 and analysis results are permanently stored, such as in the patient's medical records. For example, the ECG monitoring system 1 may transmit the ECG dataset 40 to a host network for the medical facility which houses patient medical records and/or an ECG database, such as a MUSE ECG management system housing ECG waveform data and available by General Electric Company of Schenectady, N.Y. Alternatively, the ECG dataset and analysis results may be printed as a permanent graphical record or in addition to electronic storage or transmission.

Returning to FIG. 2, one embodiment of the computing system 100 in the monitor 4 includes rapid acquisition module 11 executable to rapidly acquire an ECG test of a specified duration as described herein. The computing system 100 includes a processor 106, storage system 104, software 102, and communication interface 108. The processing system 106 loads and executes software 102 from the storage system 104, including the rapid acquisition module 11. The rapid acquisition module 11 includes computer-readable instructions that, when executed by the computing system 100 (including the processor 106), direct the processing system 106 to operate as described in herein in further detail, including to execute the steps shown and described with respect to FIGS. 3 and 4A-4B.

Figure 2:
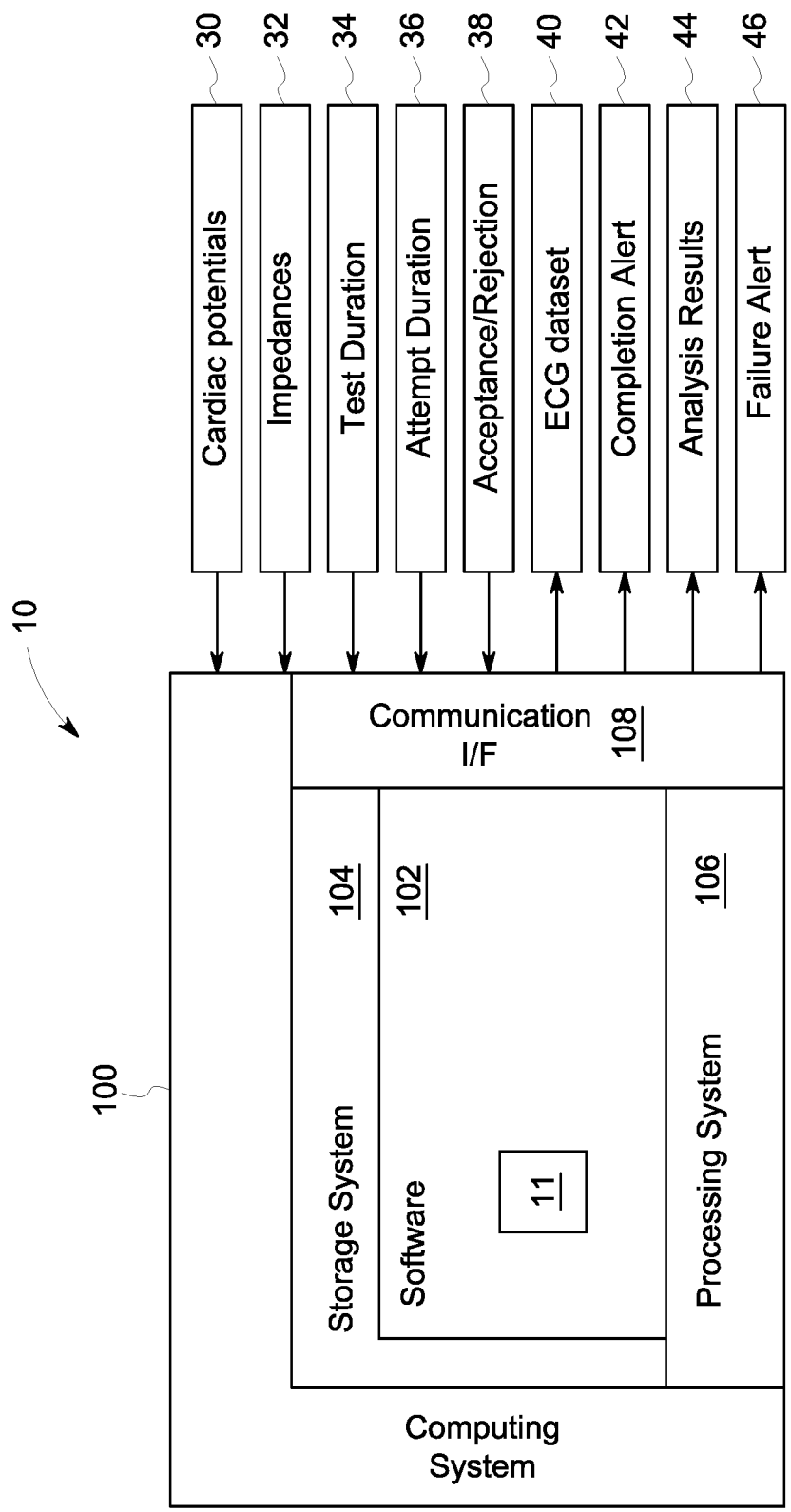
FIG. 2 depicts one embodiment of a computing system incorporated in an ECG monitoring system according to the present disclosure.

Although the computing system 100 as depicted in FIG. 2 includes one software 102 encapsulating one rapid acquisition module 11, it should be understood that one or more software elements having one or more modules may cooperate to provide the same operation. Similarly, while the description as provided herein refers to a single computing system 100 and a processor 106, it is to be recognized that implementations of such systems can be performed using one or more processors, which may be communicatively connected, and such implementations are considered to be within the scope of the description.

The processor 106 can comprise a microprocessor and other circuitry that retrieves and executes software 102 from storage system 104. Processor 106 can be implemented within a single processing device but can also be distributed across multiple processing devices or sub-systems that cooperate in executing program instructions. Examples of processor 106 include general purpose central processing units, applications specific processors, and logic devices, as well as any other type of processing device, combinations of processing devices, or variations thereof.

The storage system 104 can comprise any storage media, or group of storage media, readable by processor 106, and capable of storing software 102. The storage system 104 can include volatile and non-volatile, removable and non-removable media implemented in any method or technology for storage of information, such as computer-readable instructions, data structures, program modules, or other data. Storage system 104 can be implemented as a single storage device but may also be implemented across multiple storage devices or sub-systems. For example, the software 102 may be stored on a separate storage device than the ECG dataset 40. Storage system 104 can further include additional elements, such a controller capable of communicating with the processing system 106.

Examples of storage media include random access memory, read only memory, magnetic discs, optical discs, flash memory, virtual memory, and non-virtual memory, magnetic sets, magnetic tape, magnetic disc storage or other magnetic storage devices, or any other medium which can be used to storage the desired information and that may be accessed by an instruction execution system, as well as any combination or variation thereof, or any other type of storage medium. Likewise, the storage media may be housed locally with the processing system 106, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 108 may comprise any elements and/or circuitry necessary to communicate with the other devices in the system 1, including the user interface 14 and the signal processing circuit 112. The user interface 14 is generally any device, or group of devices, configured to provide information to the clinician, such as a visual depiction of the ECG dataset 40, the completion alert 42, analysis results 44, and failure alert 46. Furthermore, the user interface 14 is configured to receive input from a clinician or other user of the ECG monitoring system 1, such as to include input selecting the test duration 34, attempt duration 36, and/or an acceptance or rejection 38 of an ECG dataset 40. The user interface 14 may include any means for inputting such information. To provide just a few examples, the user interface 14 may receive user input through a touch screen, such as comprising the display 15, a mouse, a keyboard, a voice input device, a touch input device other than the touch screen, a visual input device for detecting non-touch motion and/or gestures by a user, and/or any other comparable input devices and associated processing elements capable of receiving input from a user, such as a clinician. Output devices include a display 15, which may be any video display or graphical display, numerous embodiments of which are known and available in the art. Output devices further include the speaker 17 for providing an audio alert to a clinician, such as part of the completion alert 42 and/or the failure alert 46.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. An ECG monitoring system comprising:
   two or more electrodes configured to record cardiac potentials from a patient;
   a display;
   at least one processor;
   a rapid acquisition module executable on the at least one processor to:
      determine an impedance of the two or more electrodes and compare each impedance to an impedance threshold;
      start a settling timer, using the processor, once the impedance of the two or more electrodes is less than the impedance threshold;
      generate ECG lead data based on the cardiac potentials;
      repeatedly assess the ECG lead data to determine whether a noise level requirement and an impedance level requirement have been met;
      identify an ECG dataset from the ECG lead data when the noise level requirement and the impedance level requirement are met for at least a predetermined test duration;
      when the settling timer reaches a predetermined attempt duration where the noise level requirement and the impedance level requirement have not been met for at least the predetermined test duration, reassess the ECG lead data generated during the attempt duration to identify at least one alternative ECG dataset from the ECG lead data; and
      display on the display at least a portion of the ECG dataset or the at least one alternative ECG dataset and/or an alert that the ECG dataset has been identified.

2. The system of claim 1, wherein the rapid acquisition module is further executable on the processor to modify at least the noise level requirement, wherein reassessing the ECG lead data includes determining whether the modified noise level requirement has been met for at least the predetermined test duration to identify the at least one alternative ECG dataset.

3. The system of claim 1, wherein the rapid acquisition module is further executable on the processor to stop the settling timer once the ECG dataset is identified.

4. The system of claim 3, wherein the rapid acquisition module is further executable on the processor to generate a failure alert after the settling timer reaches the predetermined attempt duration.

5. The system of claim 1, wherein the impedance level requirement includes that the impendence of all electrodes remains less than the impedance threshold.

6. The system of claim 1, wherein the noise level requirement includes that the noise level in at least a subset of leads is maintained below the noise threshold for the predetermined test duration while the impedance level requirement is met.

7. The system of claim 1, wherein the rapid acquisition module is further executable on the processor to continually determine whether the noise level requirement and the impedance level requirement are met, and to identify the ECG dataset from the ECG lead data as soon as the noise level requirement and the impedance level requirement are simultaneously met for the predetermined test duration.

8. A computer-implemented method of monitoring ECG, the method comprising:
   determining that an impedance of each of two or more electrodes is less than an impedance threshold;
   recording cardiac potentials from the two or more electrodes;
   generating with a processor ECG lead data based on the cardiac potentials;
   starting a settling timer with the processor once the impedance of the two or more electrodes is less than an impedance threshold;
   repeatedly assessing the ECG lead data with the processor to determine whether a noise level requirement and an impedance level requirement have been met;
   identifying an ECG dataset from the ECG lead data with the processor when the noise level requirement and the impedance level requirement are met for at least a predetermined test duration;
   when the settling timer reaches a predetermined attempt duration where the noise level requirement and the impedance level requirement have not been met for at least the predetermined test duration, reassessing the ECG lead data generated during the attempt duration with the processor to identify at least one alternative ECG dataset from the ECG lead data; and
   displaying at least a portion of the ECG dataset or the at least one alternative ECG dataset and/or an alert that the ECG dataset has been identified.

9. The method of claim 8, further comprising modifying at least the noise level requirement, wherein reassessing the ECG lead data includes determining whether the modified noise level requirement has been met for at least the predetermined test duration to identify the at least one alternative ECG dataset.

10. The method of claim 8, further comprising receiving user input accepting or rejecting of the ECG dataset and, upon receiving a rejection, restarting the settling timer and recording new ECG data for the predetermined attempt duration to identify at least one alternative ECG dataset.

11. The method of claim 8, further comprising stopping the settling timer once the ECG dataset is identified.

12. The method of claim 11, further comprising generating a failure alert after the settling timer reaches the predetermined attempt duration.

13. The method of claim 8, wherein the noise level requirement includes that the noise level in at least a subset of leads is maintained below the noise threshold for the predetermined test duration while the impedance requirement is met.

14. The method of claim 13, wherein the impedance level requirement includes that the impendence of all electrodes remains less than the impedance threshold.

15. The method of claim 8, further comprising continually determining whether the noise level requirement and the impedance level requirement are met, and to identify the ECG dataset from the ECG lead data as soon as the noise level requirement and the impedance level requirement are simultaneously met for the predetermined test duration.

* * * * *